United States Patent [19]
Balzer et al.

[11] Patent Number: 5,637,115
[45] Date of Patent: Jun. 10, 1997

[54] OXIDATION HAIR DYE COMPOSITIONS CONTAINING DEVELOPERS, COUPLERS, AND AZO DYES

[75] Inventors: Wolfgang R. Balzer, Alsbach, Germany; Hans-Juergen Braun, Ueberstorf, Switzerland

[73] Assignee: Wella Aktiengesellschat, Darmstadt, Germany

[21] Appl. No.: 586,300

[22] Filed: Jan. 16, 1996

[30] Foreign Application Priority Data

Apr. 29, 1995 [DE] Germany ............ 195 15 903.9

[51] Int. Cl.$^6$ ............................ A61K 7/13
[52] U.S. Cl. ............ 8/407; 8/408; 8/409; 8/410; 8/411; 8/412; 8/423
[58] Field of Search ............ 8/405, 406, 407, 8/408, 409, 410, 411, 412, 416, 423

[56] References Cited

U.S. PATENT DOCUMENTS

| | | | |
|---|---|---|---|
| 3,368,941 | 2/1968 | Boosen | 8/407 |
| 4,025,301 | 5/1977 | Lang | 8/426 |
| 4,289,495 | 9/1981 | Bugaut et al. | 8/406 |
| 4,886,517 | 12/1989 | Bugaut et al. | 8/414 |
| 5,226,924 | 7/1993 | Junino et al. | 8/429 |
| 5,409,502 | 4/1995 | Braun | 8/429 |

FOREIGN PATENT DOCUMENTS

| | | |
|---|---|---|
| 543288 | 2/1932 | Australia. |
| 601302 | 6/1994 | European Pat. Off.. |
| 3942315 | 6/1991 | Germany. |
| 4219738 | 12/1993 | Germany. |

OTHER PUBLICATIONS

Hair Dyes, J.C. Johnson, 1973, pp. 1–139.

*Primary Examiner*—Paul Lieberman
*Assistant Examiner*—Caroline L. Dusheck
*Attorney, Agent, or Firm*—Michael J. Striker

[57] ABSTRACT

The oxidation hair dye composition consists of a combination of 0.01 to 10 percent by weight of one or more developer substances and 0.01 to 5 percent by weight of one or more coupler substances, and 0.01 to 2 percent by weight of one or more azo dye compounds of the formula I, A—N=N—B, wherein A is a p-aminophenyl group or a 3-pyridyl group and B is a 2,6-diamino-3-pyridyl group or a substituted 4-[N,N-bis-(2'-hydroxyethyl)amino]phenyl group of formula IV:

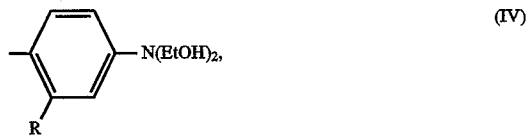

(IV)

wherein R is hydrogen, an alkyl group having from 1 to 6 carbon atoms, fluorine, chlorine, bromine or iodine; and one or more cosmetic additive selected from the group consisting of solvents, surfactants, antioxidants, thickeners, pH-adjusting compounds, hair care materials and additional dye components. The additional dye components can be 6-amino-2-methylphenol, 2-amino-5-methylphenol, triphenylmethane dye compounds and/or aromatic nitro dye compounds.

23 Claims, No Drawings

OXIDATION HAIR DYE COMPOSITIONS CONTAINING DEVELOPERS, COUPLERS, AND AZO DYES

BACKGROUND OF THE INVENTION

The present invention relates to a composition for oxidative dyeing of hair based on a combination of developer and coupler substances and based on a yellow to yellow-orange azo dye compound.

Oxidation hair dyes have attained substantial importance in hair dye practice. The hair dye is produced by oxidative coupling of developer substance and coupler substance on the hair shaft. This leads to a very intensive hair dyeing with very good color fastness.

Advantageously 2,5-diaminotoluene, 1,4-diaminobenzene, 2-(2'-hydroxyethyl)-1,4-diaminobenzene, 4-aminophenol, 4-amino-2-aminomethylphenol and 4-amino-3-methylphenol and substituted 4,5-diaminopyrazoles can be used as developer substances.

m-phenylenediamine and its derivatives, such as 2,4-diaminophenoxyethanol, 2,4-diamino-5-fluorotoluene and 2-amino-4-(2'-hydroxyethyl)aminoanisole, or pyridine derivatives such as 3,5-diamino-2,6-dimethoxypyridine as blue couplers; 1-naphthol, m-aminophenol and its derivatives, such as 2-amino-4-chloro-6-methylphenol, 5-amino-2-methylphenol, 4-amino-2-hydroxyphenoxyethanol, 4-amino-5-fluoro-2-hydroxytoluene and 4-amino-5-ethoxy-2-hydroxytoluene as red couplers; and resorcinol, 4-chlororesorcinol, 4,6-dichlororesorcinol, 2-methylresorcinol, 4-hydroxy-1,2-methylenedioxybenzene, 4-(2'-hydroxyethyl)amino-1,2-methylenedioxybenzene and 4-hydroxyindole as couplers for brown-blond shades; are all advantageously used as coupler substances in oxidation hair dye compositions.

Many different color shades or tones which fulfill the standard requirements for hair dyeing can be obtained by a suitable combination of individual developer and coupler substances.

Certain color shades however can be obtained only with great difficulty using oxidation hair dye compounds. It is extraordinarily difficult to obtain fashionable shades in the gold region with oxidation hair dye compounds.

According to the hair structure and dyeing conditions, which in practice necessarily fluctuate, color shifts occur in hair dyeing with oxidation hair dye compositions. The resulting different hair colors, which are usually green tinged and/or orange tinged, are unpleasing to customers and partially unacceptable.

SUMMARY OF THE INVENTION

It is an object of the present invention to provide an oxidation hair dye composition for dyeing hair in a plurality of different color shades or tones including the fashionable shades in the gold region, in which the disadvantageous color shifts mentioned above do not occur or occur only to a very slight extent.

It has now been found unexpectedly that this object is attained in an outstanding way by an oxidation hair dye composition based on a developer-coupler combination and certain yellow to yellow-orange azo dyes.

According to the invention an oxidation hair dye composition for oxidative dyeing of hair contains a combination of at least one coupler substance and at least one developer substance and includes at least one azo dye compound of the formula I,

in which A is a p-aminophenyl group of the formula (II) or a 3-pyridyl group of the formula (III):

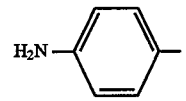

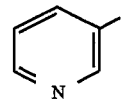

wherein B is a 4-[N,N-bis-(2'-hydroxyethyl)amino]phenyl group of the formula IV:

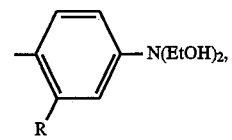

wherein R is hydrogen, an alkyl group with from 1 to 6 carbon atoms, fluorine, chlorine, bromine or iodine, or B is a 2,6-diamino-3-pyridyl group of the formula V:

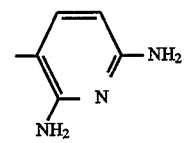

In a preferred embodiment of the invention in the compositions according to the invention the at least one azo dye compound of the formula I has an A group according to the formula II or the formula III, if the B group is according to the formula V, but has an A group according to the formula II, if the B group is the B Group according to the formula IV.

The following compounds are especially suitable as azo dye compounds: 4-amino-4'-[N,N-bis-(2"-hydroxyethyl)amino]azobenzene, 4-amino-2'-methyl-4'-[N,N-bis-(2"-hydroxyethyl)amino]azobenzene, 4-amino-2'-chloro-4'-[N,N-bis-(2"-hydroxyethyl)amino]azobenzene and 2,6-diamino-3-[3'-azopyridyl]-pyridine.

The azo dye compounds of formula I can be used in the hair dye composition according to the invention individually and also in a mixture with each other. The total amount of these compounds advantageously amounts to from about 0.01 to 2 percent by weight. An amount of from about 0.05 to 0.5 percent by weight of the azo dye compound of formula I is particularly preferred.

The developer substance for the hair dye composition according to the invention can include one or more of the following: 1,4-diaminobenzene, 2,5-diaminotoluene, 2-(2'-hydroxyethyl)-1,4-diaminobenzene, 4-aminophenol, 4-amino-2-aminomethylphenol, 4-amino-3-methylphenol, 4-amino-2-methoxymethylphenol, 4-amino-2-ethoxymethylphenol, 4,5-diamino-1-methylpyrazole, 4,5-diamino-1-isopropyl pyrazole, 1-benzyl-4,5-diamino pyrazole, 4,5-diamino-1-(4'-methylbenzyl)pyrazole and tetraaminopyrimidine.

These developer substances can be used alone, or in a mixture with each other, and are contained in the hair dye composition according to the invention advantageously in an amount of from 0.01 to 10 percent by weight, particularly advantageously however from 0.05 to 5.0 percent by weight.

The coupler substance in the hair dye composition according to the invention can include one or more of the following coupler compounds: resorcinol, 4-chlororesorcinol, 4,6-dichlororesorcinol, 2-methylresorcinol, 2-amino-4-(2'-hydroxyethylamino)anisole, 2,4-diamino-5-fluorotoluene, m-phenylenediamine, 5-amino-2-methylphenol, 2,4-diaminophenoxyethanol, 1-naphthol, m-aminophenol, 3-amino-4-chloro-6-methylphenol, 3-amino-2-methylphenol, 4-amino-2-hydroxyphenoxyethanol, 4-amino-5-fluoro-2-hydroxytoluene, 4-amino-5-ethoxy-2-hydroxytoluene, 4-hydroxy-1,2-methylenedioxybenzene, 4-(2'-hydroxyethylamino)-1,2-methylenedioxybenzene, 2,4-diamino- 5-ethoxytoluene, 4-hydroxyindole and 3,5-diamino-2,6-dimethoxypyridine.

The coupler substance can be contained in the oxidation hair dye composition according to the invention in an amount from 0.01 to 5 percent by weight, advantageously 0.05 to 3 percent by weight.

The total amount of the developer-coupler combination contained in the hair dye composition described here should amount to from about 0.1 to 6 percent by weight, but from about 0.5 to 4.0 percent by weight is particularly preferred. The developer substances are used generally in about equimolar quantities, relative to the coupler substances. It is however not disadvantageous when the developer substances are present in a certain excess relative to the coupler substances present or when the coupler substance is present in excess relative to the developer substances.

Furthermore direct dyes can also be included in the hair dye compositions according to the invention. These direct dyes can include, for example, 6-amino-2-methylphenol and 2-amino-5-methylphenol as well as additional conventional direct dyes, for example triphenylmethane dye compounds, such as 4-[(4'-aminophenyl)-(4"-imino-2",5"-cyclohexadien-1"-yliden)methyl]-2-methylaminobenzene monohydrochloride, otherwise known as Basic Violet 14 (C.I. 42 510), 4-[(4'-amino-3'-methylphenyl)-(4"-imino-3"-methyl-2",5"-cyclohexadien-1"-yliden)methyl]-2-methylaminobenzene monohydrochloride, otherwise known as Basic Violet 2 (C.I. 42 520), aromatic nitro dye compounds such as 2-amino-4,6-dinitrophenol, 2-amino-5-(2'-hydroxyethylamino)-nitrobenzene and 4-(2'-hydroxyethylamino)-3-nitrotoluene, 1-(2'-ureidoethyl) amino-4-nitrobenzene and azo dye compounds, such as 7-[(4'-aminophenyl)azo]-8-hydroxynaphthalen-4-sulfonic acid sodium salt, otherwise known as Acid Brown 4 (C.I. 14 805), and disperse dye compounds, such as 1,4-diaminoanthraquinone and 1,4,5,8-tetraaminoanthraquinone. These direct dye compounds can be included in the hair dye composition according to the invention in amounts of from 0.1 to 4.0 percent by weight.

Additional hair dye compounds suitable for the hair dye compositions according to the invention are described, for example, in the book by J. C. Johnson, "Hair Dyes", Noyes Data Corp., Park Ridge, USA (1973), pp. 3 to 91 and 113 to 129 (ISBN: 0-8155-0477-2).

The coupler and developer substances and the other dye components, in so far as they are bases, can be used understandably also in the form of physiologically acceptable or compatible acid addition salts, for example as their hydrochlorides or sulfates, or—in so far as they have aromatic OH groups—in the form of salts with bases, for example as an alkali metal phenolate.

Furthermore the hair dye compositions according to the invention can include antioxidants, such as ascorbic acid, sodium bisulfite, sodium sulfite or thioglycolic acid. These antioxidants are advantageously present in an amount of from about 0.1 to 1.5 percent by weight. The use of ascorbic acid, sodium sulfite and especially sodium bisulfite is particularly preferred.

The preparation used can be for example in the form of a solution, especially an aqueous-alcoholic solution. The particularly preferred forms of the preparation are however a cream, a gel or an emulsion.

The composition of the preparation comprises a mixture of the above-described dye components with the conventional additives used in this type of cosmetic preparation.

Additional standard additives for hair dye compositions according to the invention in the form of solutions, creams, emulsions or gels include, for example, solvents such as water, lower aliphatic alcohols such as ethanol, propanol, isopropanol and glycerol, or glycols, such as 1,2-propylene glycol; wetting agents or emulsifiers chosen from the categories of anionic, cationic, amphoteric or nonionic surface active substances, such as fatty alcohol sulfates, ethoxylated fatty alcohol sulfates, alkylsulfonates, alkylbenzene sulfonates, alkyltrimethylammonium salts, alkylbetains, ethoxylated fatty alcohols, ethoxylated nonylphenol, fatty acid alkanol amides, ethoxylated fatty acid esters; thickeners, such as higher fatty alcohols, starches, cellulose derivatives, Petrolatum (Vaseline®), paraffin oil and fatty acids as well as hair care materials, such as cationic resins, lanolin derivatives, cholesterol, pantothenic acids and betaine. The above-mentioned conventional components are used in amounts which are standard for their particular purpose, e.g. the wetting agents and emulsifiers in concentrations of about 0.5 to 30 percent by weight, the thickeners in amounts of from about 0.1 to 25 percent by weight and the hair care materials in a concentration of about 0.1 to 5.0 percent by weight.

The hair dye composition according to the invention can be weakly acidic, neutral or alkaline according to its composition. The pH of the hair dye composition particularly can be from 6.0 to 11.5. The pH of the composition can be adjusted successfully with ammonia, but it can also be adjusted with an organic amine, for example monoethanolamine and triethanolamine, or also an inorganic base, such as sodium hydroxide and potassium hydroxide. For a pH adjustment in the acid region, for example, phosphoric acid, acetic acid, citric acid or tartaric acid can be used.

The method of using the oxidation hair dye composition according to the invention includes mixing the above-described hair dye composition immediately prior to use with an oxidizing agent and applying the mixture to the hair in a sufficient amount to dye the hair, according to the amount of hair present, generally in an amount of from 60 to 200 g.

The oxidizing agent or composition for developing the hair dye includes principally hydrogen peroxide or its addition compounds with urea, melamine or sodium borate in the form of a 3 to 12 percent, advantageously 6 percent, aqueous solution. However air oxygen can also be used. Similarly it is possible to develop the color by action of atmospheric oxygen, which means without addition of an oxidizing agent. If a 6-percent hydrogen peroxide solution is used, the weight ratio of hair dye composition according to the invention and oxidizing agent amounts to 5:1 to 1:2, advantageously however 1:1. Comparatively larger amounts of oxidizing agent are used particularly when there is a high dye compound concentration in the oxidation hair dye composition or when at the same time a comparatively stronger bleaching of the hair is intended.

In the method of using the hair dye composition according to the invention the mixture of the oxidizing agent and the hair dye composition is allowed to act on the hair at 15° to 50° C. for from 10 to 45 minutes, advantageously 30 minutes, the hair is rinsed with water and dried. If necessary in connection with the rinsing a shampoo is used to wash the hair and eventually an after-rinse is performed with a weak organic acid, such as citric acid or tartaric acid. Subsequently the hair is dried.

The hair dye compositions according to the invention provide hair colors of outstanding fastness properties, particular an outstanding light fastness, wash fastness and friction fastness and they may be removed with reducing agents. They also provide a broad palette of different hair color shades and nuances according to their type and composition, especially fashionable gold shades. Finally dyeing of gray and chemically undamaged hair is problem-free when the hair dye compositions according to the invention are used and a very good color coverage is obtained. The colors produced using the hair dye compositions according to the invention are both uniform and very satisfactorily reproducible independently of the differing hair structures to which they are applied.

The azo dye compound of formula I are produced in good yield by simple chemical reactions, for example according to the methods described in German Patent DE-PS 543 288 or German Published Patent Application DE-OS 4 219 738, and have an exceptional stability to reducing agents.

The following examples should illustrate the preferred embodiments without limiting the claims appended hereinbelow.

EXAMPLES

Examples of Hair Dye Compositions

| Example 1 | Hair Dye Gel Composition |
| --- | --- |
| 1.0 g | 4-aminophenol |
| 0.4 g | α-naphthol |
| 0.4 g | 3-amino-6-methyl-phenol |
| 0.3 g | 2,6-diamino-3-[3'-azopyridyl]pyridine |
| 0.1 g | resorcinol |
| 0.1 g | 2,5-diaminotoluene sulfate |
| 15.0 g | oleic acid |
| 8.0 g | isopropanol |
| 6.0 g | ammonia (25 percent by weight aqueous solution) |
| 3.0 g | glycerol |
| 0.3 g | ascorbic acid |
| 0.1 g | sodium bisulfite |
| 65.3 g | water |
| 100.0 | |

20 g of the above hair dye gel composition are mixed with 20 g of a 9% by weight hydrogen peroxide solution. Subsequently the mixture so obtained is applied to gray human hair and allowed to act on the hair for an acting time of thirty minutes at 40° C. The hair is then rinsed with water and dried.

A dark golden blond hair color results.

If the 2,6-diamino-3-[3'-azopyridyl]pyridine in the above-mentioned hair dye composition is replaced by an equal amount of water and the above dyeing treatment is repeated, i.e. applied to another portion of gray human hair, a dull and lifeless, hair unpleasant hair color results.

| Example 2 | Hair Dye Cream Composition |
| --- | --- |
| 0.32 g | 2,5-diaminotoluene sulfate |
| 0.30 g | 4-amino-4'-[N,N-bis-(2"-hydroxyethyl)amino]azobenzene |
| 0.20 g | 2-amino-6-chloro-4-nitrophenol |
| 0.18 g | 2,6-dihydroxytoluene |
| 15.00 g | a mixture of cetyl stearyl alcohol and sodium lauryl sulfate (90:10) (Lanette$^R$ of Henkel kGaA/Germany) |
| 3.50 g | sodium diglycol lauryl ether sulfate (20-percent aqueous solution) |
| 2.40 g | sodium hydroxide (20% aqueous solution) |
| 0.40 g | sodium bisulfite |
| 0.20 g | ascorbic acid |
| 0.20 g | monoethanolamine |
| 77.30 g | water |
| 100.0 | |

10 g of the above-described hair dye cream composition are mixed with 20 g of a 2% by weight hydrogen peroxide solution to obtain a ready-to-use hair dyeing preparation with a pH of 6.8. Subsequently the preparation so obtained is applied to gray human hair and allowed to act on the hair for an acting time of thirty minutes at 40° C. as in Example 1. The hair is then rinsed with water and dried. A brilliant shimmering golden blond shade results.

All percentages described above are percentages by weight, unless otherwise indicated.

While the invention has been illustrated and described as embodied in hair dye composition, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. An oxidation hair dye composition consisting of a combination of 0.01 to 10 percent by weight of at least one developer substance and 0.01 to 5 percent by weight of at least one coupler substance, and 0.01 to 2 percent by weight of at least one azo dye compound of the formula I,

wherein A is selected from the group consisting of a p-aminophenyl group of formula (II) and a 3-pyridyl group of formula (III):

and wherein B is selected from the group consisting of a 2,6-diamino-3-pyridyl group of formula V:

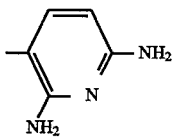

and 4-[N,N-bis-(2'-hydroxyethyl)amino]phenyl groups of formula IV:

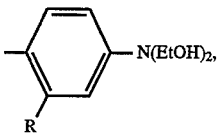

wherein R is selected from the group consisting of hydrogen, alkyl groups having from 1 to 6 carbon atoms, fluorine, chlorine, bromine and iodine; and at least one cosmetic additive selected from the group consisting of solvents, surfactants, antioxidants, thickeners, pH-adjusting compounds, hair care materials and additional dye components, wherein said additional dye components are selected from the group consisting of 6-amino-2-methylphenol, 2-amino-5-methylphenol, triphenylmethane dye compounds and aromatic nitro dye compounds.

2. The oxidation hair dye composition as defined in claim 1, wherein the at least one azo dye compound of the formula I has said p-aminophenyl group according to the formula II, if said B is said 4-[N,N-bis-(2'-hydroxyethyl)amino]phenyl group according to the formula IV, but has said A is said group according to the formula II or said group according to the formula III, if said B is said 2,6-diamino-3-pyridyl group of formula V.

3. The oxidation hair dye composition as defined in claim 1, wherein the at least one azo dye compound of the formula I is selected from the group consisting of 4-amino-4'-[N,N-bis-(2"-hydroxyethyl)amino]azobenzene, 4-amino-2'-methyl-4'-[N,N-bis-(2"-hydroxyethyl)amino]azobenzene, 4-amino-2'-chloro-4'-[N,N-bis-(2"-hydroxyethyl)amino]-azobenzene and 2,6-diamino-3-[3'-azopyridyl]pyridine.

4. The oxidation hair dye composition as defined in claim 1, having a total content of said at least one developer substance and said at least one coupler substance of from 0.1 to 6 percent by weight.

5. The oxidation hair dye composition as defined in claim 1, containing at least one of said antioxidants in an amount of from 0.1 to 15 percent.

6. The oxidation hair dye composition as defined in claim 1, wherein said antioxidants are selected from the group consisting of ascorbic acid, thioglycolic acid, sodium sulfite and sodium bisulfite.

7. The oxidation hair dye composition as defined in claim 1, wherein said solvents are selected from the group consisting of water, ethanol, propanol, isopropanol, glycerol and 1,2-propylene glycol.

8. The oxidation hair dye composition as defined in claim 1, wherein the surfactants are selected from the group consisting of wetting agents and emulsifiers.

9. The oxidation hair dye composition as defined in claim 1, containing at least one of the surfactants in an amount of from 0.5 to 30 percent by weight.

10. The oxidation hair dye composition as defined in claim 1, wherein the surfactants are selected from the group consisting of fatty alcohol sulfates, ethoxylated fatty alcohol sulfates, alkylsulfonates, alkylbenzene sulfonates, alkyltrimethylammonium salts, alkylbetains, ethoxylated fatty alcohols, ethoxylated nonylphenol, fatty acid alkanol amides and ethoxylated fatty acid esters.

11. The oxidation hair dye composition as defined in claim 1, containing at least one of said thickeners in an amount of from 0.1 to 25 percent by weight.

12. The oxidation hair dye composition as defined in claim 1, wherein said thickeners are selected from the group consisting of higher fatty alcohols, starches, cellulose derivatives, petrolatum, paraffin oil and fatty acids.

13. The oxidation hair dye composition as defined in claim 1, containing at least one of said hair care materials in an amount of from 0.1 to 5 percent by weight.

14. The oxidation hair dye composition as defined in claim 1, wherein said hair care materials are selected from the group consisting of cationic resins, lanolin derivatives, cholesterol, pantothenic acids and betaine.

15. The oxidation hair dye composition as defined in claim 1, wherein said pH adjusting compounds are selected from the group consisting of ammonia, monoethanolamine, triethanolamine, sodium hydroxide, potassium hydroxide, phosphoric acid, acetic acid, citric acid and tartaric acid.

16. The oxidation hair dye composition as defined in claim 1, containing at least one of said additional dye component in an amount of from 0.1 to 4 percent by weight.

17. The oxidation hair dye composition as defined in claim 1, wherein said at least one coupler substance is selected from the group consisting of resorcinol, 4-chlororesorcinol, 4,6-dichlororesorcinol, 2-methylresorcinol, 2-amino-4-(2'-hydroxyethylamino) anisole, 2,4-diamino-5-fluorotoluene, m-phenylenediamine, 5-amino-2-methylphenol, 2,4-diaminophenoxyethanol, 1-naphthol, m-aminophenol, 3-amino-4-chloro-6-methylphenol, 3-amino-2-methylphenol, 4-amino-2-hydroxyphenoxyethanol, 4-amino-5-fluoro-2-hydroxytoluene, 4-amino-5-ethoxy-2-hydroxytoluene, 4-hydroxy-1,2-methylenedioxybenzene, 4-(2'-hydroxyethylamino)-1,2-methylenedioxybenzene, 2,4-diamino-5-ethoxytoluene, 4-hydroxyindole and 3,5-diamino-2,6-dimethoxypyridine.

18. The oxidation hair dye composition as defined in claim 1, wherein said at least one developer substance is selected from the group consisting of 1,4-diaminobenzene, 2,5-diaminotoluene, 2-(2'-hydroxyethyl)-1,4-diaminobenzene, 4-aminophenol, 4-amino-2-aminomethylphenol, 4-amino-3-methylphenol, 4-amino-2-methoxymethylphenol, 4-amino-2-ethoxymethylphenol, 4,5-diamino-1-methylpyrazole, 4,5-diamino-1-isopropyl pyrazole, 1-benzyl-4,5-diamino pyrazole, 4,5-diamino-1-(4'-methylbenzyl)pyrazole and tetraaminopyrimidine.

19. The oxidation hair dye composition as defined in claim 1, consisting of an aqueous or aqueous-alcoholic preparation in the form of a solution, cream or gel.

20. A method of oxidative dyeing of hair, said method comprising the steps of:
a) mixing an oxidation hair dye composition with an oxidizing agent-containing composition to form a ready-to-apply hair dyeing mixture;
b) applying the ready-to-apply hair dyeing mixture to hair to be dyed in an amount sufficient for dyeing of the hair and allowing the ready-to-apply hair dyeing mixture to act on the hair for from 10 to 45 minutes at a temperature of from 15° to 50° C.;

c) after the applying and allowing of the hair dyeing mixture in step b), rinsing the hair with water and then drying the hair;

wherein said oxidation hair dye composition consists of a combination of 0.01 to 10 percent by weight of at least one developer substance and 0.01 to 5 percent by weight of at least one coupler substance, and 0.01 to 2 percent by weight of at least one azo dye compound of the formula I,

  (I), wherein A is selected from the group consisting of a p-aminophenyl group of formula (II) and a 3-pyridyl group of formula (III):

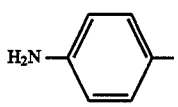 (II)

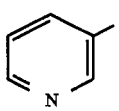 (III)

and wherein B is selected from the group consisting of a 2,6-diamino-3-pyridyl group of formula V:

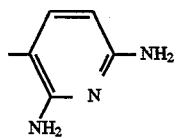 (V)

and 4-[N,N-bis-(2'-hydroxyethyl)amino]phenyl groups of formula IV:

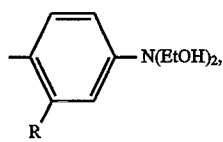 (IV)

wherein R is selected from the group consisting of hydrogen, alkyl groups having from 1 to 6 carbon atoms, fluorine, chlorine, bromine and iodine; and at least one cosmetic additive selected from the group consisting of solvents, surfactants, antioxidants, thickeners, pH-adjusting compounds, hair care materials and additional dye components, wherein said additional dye components are selected from the group consisting of 6-amino-2-methylphenol, 2-amino-5-methylphenol, triphenylmethane dye compounds and aromatic nitro dye compounds.

21. The method as defined in claim 20, wherein the oxidizing agent-containing composition includes an oxidizing agent selected from the group consisting of hydrogen peroxide, an addition compound of hydrogen peroxide and urea, an addition compound of hydrogen peroxide and melamine and an addition compound of hydrogen peroxide and sodium borate.

22. The method as defined in claim 20, wherein the oxidizing agent-containing composition consists of a 6-percent hydrogen peroxide solution and the ready-to-apply hair dyeing mixture is mixed with the oxidizing agent-containing composition in a weight ratio of from 5:1 to 1:2.

23. The method as defined in claim 20, wherein the oxidizing agent-containing composition is air and said air includes oxygen as an oxidizing agent.

* * * * *